United States Patent [19]

Boden et al.

[11] 4,390,448
[45] Jun. 28, 1983

[54] PERFUMED STABLE AQUEOUS HYPOCHLORITE BLEACH COMPOSITIONS CONTAINING 2-METHYL-2-OCTANOL AND THICKENED VARIATION THEREOF

[75] Inventors: Richard M. Boden, Monmouth Beach; Michael Licciardello, Farmingdale; Joseph J. Maisano, Jr., Wanamassa; Marie R. Hanna, Hazlet, all of N.J.

[73] Assignee: International Flavors & Fragrances Inc., New York, N.Y.

[21] Appl. No.: 313,685

[22] Filed: Oct. 22, 1981

[51] Int. Cl.$^3$ .................. C11D 7/54; C11D 3/395; C11D 3/50
[52] U.S. Cl. .................. 252/187.26; 8/108 R; 8/108 A; 252/95; 252/99; 252/174.11; 252/522 R
[58] Field of Search ............. 252/187.26, 187.25, 252/95, 99, 174.11, 522 R; 8/108 A, 108 R

[56] References Cited

U.S. PATENT DOCUMENTS

| | | | |
|---|---|---|---|
| 3,172,861 | 3/1965 | Steinhauer et al. | 252/187.26 |
| 3,560,389 | 2/1971 | Hunting | 252/187.26 |
| 4,113,645 | 9/1978 | DeSimone | 252/187.26 |
| 4,339,344 | 7/1982 | Boden et al. | 252/187.25 |
| 4,342,663 | 8/1982 | Boden et al. | 252/187.26 |

Primary Examiner—Irwin Gluck
Attorney, Agent, or Firm—Arthur L. Liberman

[57] ABSTRACT

Described is a process for producing a stable single phase aqueous alkali metal hypochlorite solution having good surface tension properties and optionally having a relatively high viscosity (5–25 centipoises at 20°–40° C.) and having a stable fragrance consisting, in sequential order, of the steps of (a) adjusting the pH of an aqueous alkali metal hypochlorite solution to the range of 11–14.0; (b) admixing a composition of matter selected from the group consisting of: (i) a chemical compound having the structure:

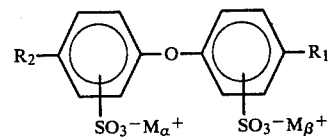

wherein at least one of $R_1$ and $R_2$ is $C_{10}$–$C_{12}$ straight chain or branched chain alkyl and $M_\alpha$ and $M_\beta$ are the same or different and each represents alkali metal selected from the group consisting of lithium, potassium and sodium; and (ii) a mixture of at least one compound having the structure:

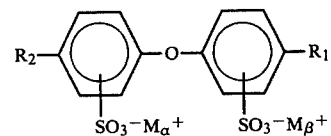

and a compound having the structure:

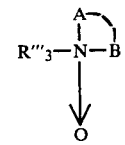

wherein $R_3'''$ is straight chain alkyl; wherein more than 55% of the $R_3'''$ moieties consist of straight chain alkyl having from 11 up to 13 carbon atoms and wherein A and B are each separately methyl or taken together complete a morpholine ring, with a perfuming quantity of 2-methyl-2-octanol whereby a premix is formed; (c) optionally adding to said premix a gel-forming agent selected from the group consisting of sodium palmitate, lithium palmitate, potassium palmitate, sodium laurate, lithium laurate, potassium laurate, sodium stearate, potassium stearate and lithium stearate; and (d) adding said premix to the pH-adjusted hypochlorite solution.

8 Claims, 8 Drawing Figures

GLC PROFILE FOR EXAMPLE I.

GLC PROFILE FOR FRACTION 4 OF EXAMPLE I.

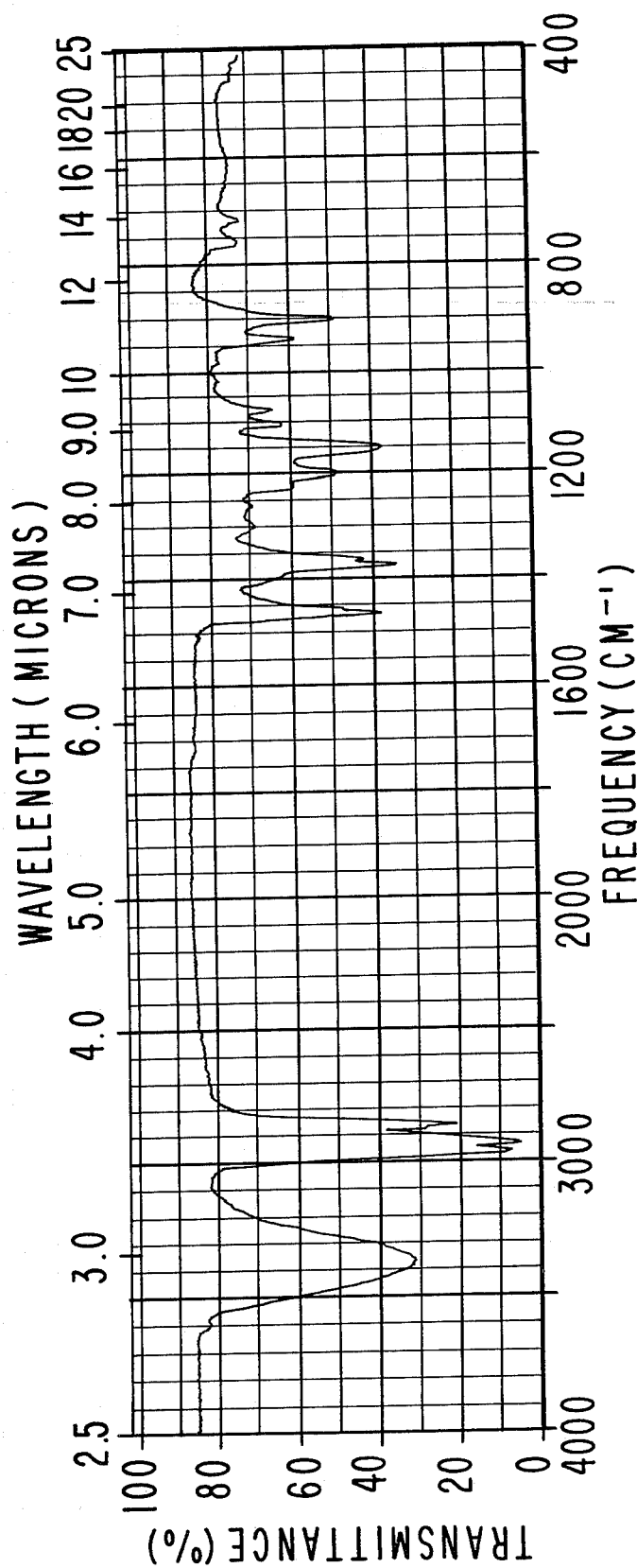

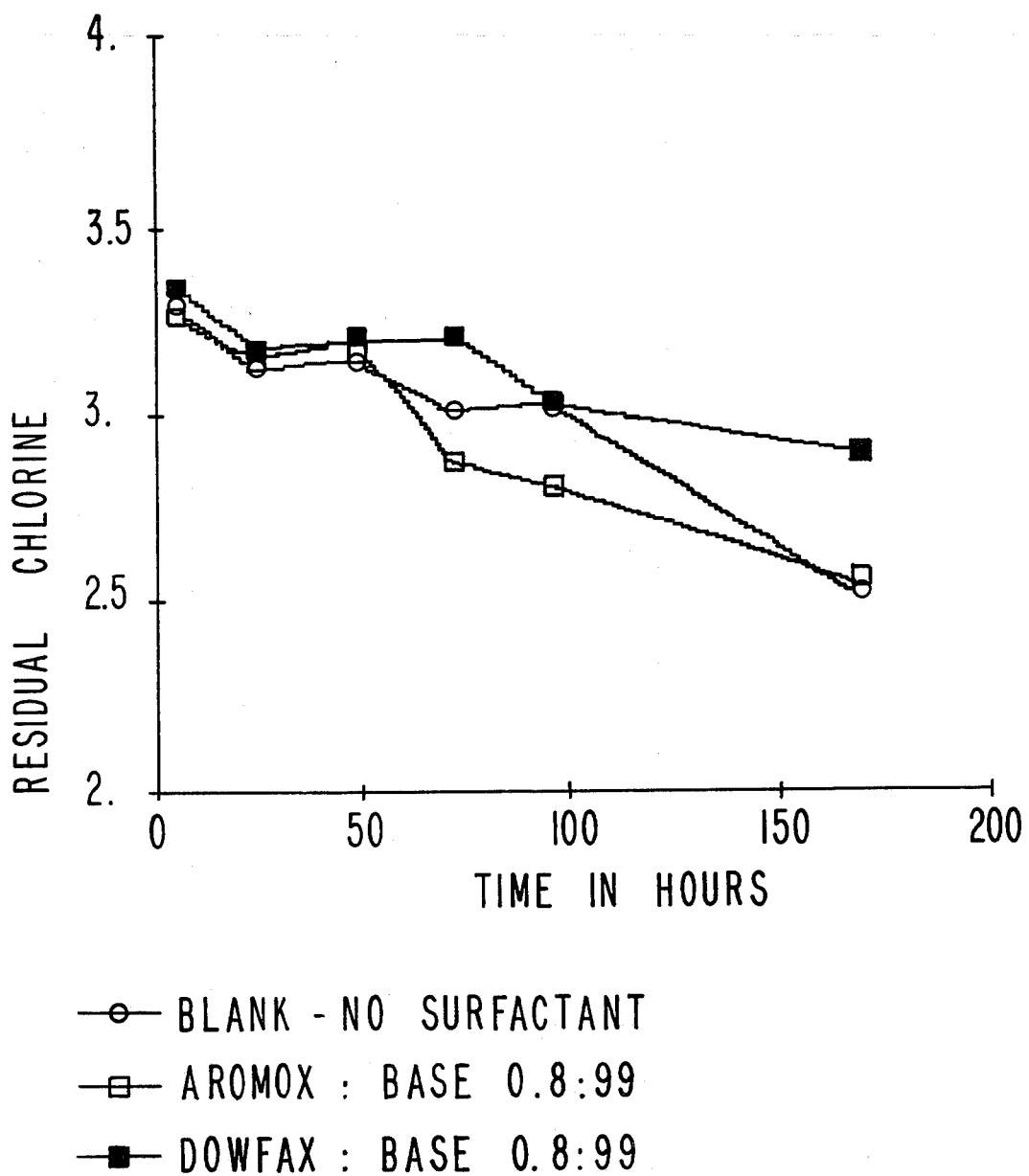

- ○ BLANK - NO SURFACTANT AND NO FRAGRANCE.
- □ DOWFAX: DIISOAMYLENE EPOXIDE + 2-METHYL-2-OCTANOL: BASE 3.8:0.2:9
- ■ DOWFAX: DIISOAMYLENE EPOXIDE + 2-METHYL-2-OCTANOL: BASE 3.8:0.2:9
- ◇ AROMOX: BASE 3.8:96 NO DIISOAMYLENE EPOXIDE OR 2-METHYL-2-OCTANOL
- ◆ DOWFAW: BASE 3.8:96 NO DIISOAMYLENE EPOXIDE OR 2-METHYL-2-OCTANOL

PERFUMED STABLE AQUEOUS HYPOCHLORITE BLEACH COMPOSITIONS CONTAINING 2-METHYL-2-OCTANOL AND THICKENED VARIATION THEREOF

BACKGROUND OF THE INVENTION

Considerable difficulties have heretofore been encountered in using such compounded hypochlorite bleach or sterilizing solutions with perfumed oils so that a stable long-lasting single phase commercially feasible bleach or sterilizing solution has been difficult to obtain, particularly wherein the desired aroma of the article bleached or sterilized (e.g., clothing) has a pleasant and stable and consistent aroma on drying (and *not* the usual "hypochlorite-bleached-article" aroma). The problem has been defined in United Kingdom Patent No. 886,084, published on Jan. 3, 1962 wherein it is stated that a stable "dispersion" of hypochlorite-resistant perfume in queous solutions of hypochlorites was formulated. United Kingdom Patent No. 886,084 discloses the preparation of an aqueous "solution" of a hypochlorite containing a hypochlorite resistant perfume and a surface active quaternary ammonium compound of the betaine type soluble in the hypochlorite solution. Such ammonium compounds have the generic structure:

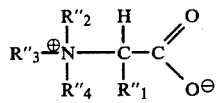

wherein each of $R_1''$, $R_2''$, $R_3''$ and $R_4''$ are alkyl. One of the features of the perfumed solutions produced in accordance with said United Kingdom Patent No. 886,084 is indicated to be that the solution exhibits foaming properties. Another feature of United Kingdom No. 886,084 is stated to be that the perfumed solutions covered by the patent are found to be clear and homogeneous after eight weeks of storage at room temperature. Nevertheless, betaines such as "Ambiteric D" as are discussed therein are not so broadly useful when used in concentrations of from 0.15% up to 4.0% (based on total weight of bleach or sterilizing solution) as to have the ability to be used in conjunction with perfume oils which should be incorporated into thickened, high viscous hypochlorite bleaches or sterilizers having excellent surface tension properties so that long lasting, stable, soluble single phase thickened perfumed aqueous alkali metal hypochlorite bleach or sterilizing solutions having long lasting pleasant stable aromas are obtained, particularly where the quantity of perfume oil in the bleach or sterilizing substance is at levels of between 0.02% and 0.8% by weight of the total bleach or sterilizing solution. The need for such aromas (e.g., "citrusy") to be present in such bleach or sterilizing solutions exists so that the disagreeable characteristic "hypochlorite" aroma is substantially eliminated from aromas of the product to which the bleach or sterilizing solution is applied; particularly on dry-out, as well as from the aroma of the hands of the user when they are in direct contact with such bleach or sterilizing solutions.

U.S. Pat. No. 3,560,389 also discloses the feasibility of using perfume oils in hypochlorite bleaches or sterilizers at column 3, lines 37–40 but the disclosure is limited to inclusion of various detergents in addition to amine oxides, such as lithium lauryl sulfate and sodium lauryl ether sulfate and/or is further limited to include hydrotropes such as sodium xylene sulfonate in addition to the amine oxide. Exclusion of such hydrotropes and detergents additional to the amine oxides and diphenyl oxide derivatives of our invention is desirable not only to cause the 2-methyl-2-octanol to function properly, but also from an ecological standpoint.

European Chemical News, Volume 13, Jan. 18, 1968, sets forth a synopsis of South African Pat. No. 67/4667 which corresponds to U.S. Pat. No. 3,560,389, but the reference also states at page 42: "Alternatively, a detergent with bleaching or bacteriocidal properties can be formulated. Perfuming bleaching solutions is now possible."

Neither the South African nor the U.S. patents, however, indicate the advantages and usefulness of limiting the detergents either to (a) compounds having the generic structure:

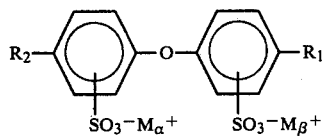

wherein at least one of $R_1$ and $R_2$ represents $C_{10}$–$C_{12}$ straight chain or branched chain alkyl and when one of $R_1$ or $R_2$ is $C_{10}$–$C_{12}$ branched or straight chain alkyl, the other or $R_1$ or $R_2$ is pH-adjusted hydrogen and wherein $M_\alpha$ and $M_\beta$ are the same or different and each represents alkali metal which may be sodium, lithium or potassium, or (b) to mixtures of compounds having the structure:

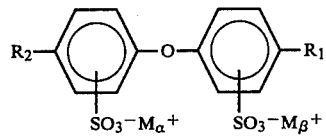

with at least one amine oxide defined according to the structure:

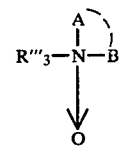

of excluding from the formulation a hydrotrope or of specifying the nature of the perfume oil useful in the perfumed bleach or sterilizing solution (wherein A and B are each separately methyl or taken together, complete a morpholino ring and wherein $R_3'''$ is straight chain alkyl having from 11 up to 13 carbon atoms).

U.S. Pat. No. 3,876,551 in attempting to solve the foregoing problem discloses a stable single phase aqueous alkali metal hypochlorite liquid perfume bleach or sterilizing composition comprising an aqueous mixture of (1) an amine oxide composition consisting essentially of at least one morpholino- and/or dimethyl ($C_{11}$–$C_{13}$ straight chain alkyl) amine oxide in an amount greater than 55% of said amine oxide composition, (2) at least one alkali metal hydroxide, (3) at least one alkali metal hypochlorite, and (4) a perfume oil compatible with the mixture capable of imparting a "woody" or a "floral" or a "clean fresh" or a "musk" or a "citrusy" note to the bleach or sterilizing composition; the mixture having a pH in the range of from 12 to 13.5 and the mixture excluding hydrotropes as well as all surfactants except the amine oxide. U.S. Pat. No. 3,876,551 also attempts to solve the foregoing problem by disclosing a process for producing the above-name mixture comprising the steps of combining an amide oxide composition consisting essentially of one or more morpholino and/or dimethyl $C_{11}$-$C_{13}$ straight chain alkyl amine oxide(s) with the perfumed oil to form an amine oxide-perfume oil premix; admixing the amine oxide-perfume oil premix with an aqueous alkali metal hypochlorite solution, and combining an alkali metal hydroxide with the solution whereby the final pH of the mixture is from 12 up to 13.5. In a further effort to solve the foregoing problem U.S. Pat. No. 3,876,551 also discloses adjustment of the pH of the aqueous metal hypochlorite solution initially to the range of 12-13.5 and then combining the resulting aqueous hypochlorite solution with the aforementioned premix. The resulting composition is indicated to cause products to which said composition is applied to have eliminated therefrom the disagreeable characteristic "hypochlorite" aroma and instead to have a "clean fresh" or "floral" or "woody" or "musk" or "citrusy" aroma to be imparted to the treated products. In addition, it is stated that the hands of the individual user after using and being in direct contact with the hypochlorite composition will not have the disagreeable characteristic "hypochlorite" aroma but instead will have a pleasant "clean fresh" or "floral" or "woody" or "musk" or "citrusy" aroma.

The disadvantage of the system of U.S. Pat. No. 3,876,551 however, concerns (a) the inability to use a thickener in the system whereby the resulting liquid has a viscosity of 5-25 centipoises at 20°-40° C. and (b) the relatively low degree of chemical stability and substantive stability of the perfume oil and of the single liquid phase system. Nothing in U.S. Pat. No. 3,876,551 indicates such a high degree of stabilities of the perfume-hypochlorite system as exists in the system of the present invention; wherein there is also included a thickener. Indeed, the stabilities using the system of the instant invention are far greater even at levels as low as 3% hypochlorite and are also relatively stable (from a standpoint of chemical stability of perfume oil, substantive stability of perfume oil and phase separation stability taken in combination with one another) at levels of as high as 10% hypochlorite in aqueous solution. Thus, the instant system gives rise to unexpected, unobvious and advantageous properties over the systems taught in the prior art.

Furthermore, nothing in the prior art including the teaching of U.S. Pat. No. 3,876,551 states either explicitly or implicitly the compatability of a thickener in the instant system, such as sodium palmitate, sodium stearate, potassium palmitate, potassium stearate, lithium palmitate, lithium stearate, lithium laurate, potassium laurate or sodium laurate whereby a stable gel (as opposed to a liquid) phase perfumed hypochlorite system or perfumed oil stabilizer emulsifier system "premix" may be produced.

The combination of the compound group having the structure:

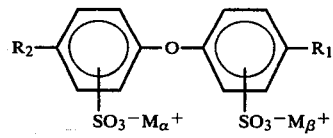

(wherein $R_1$, $R_2$, $M_\alpha$ and $M_\beta$ are defined, supra) with perfume and hypochlorite bleach in general, is set forth in the Kao Soap Company, Japanese Pat. No. 25514/79 filed on Nov. 2, 1973 and opened for public inspection on June 19, 1975. Thus, on page 2, at column 4, line 15, the compound:

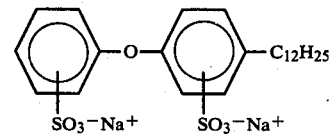

is disclosed for use in conjuntion with the perfumed hypochlorite bleaches. The claim of the Kao Soap Patent is as follows:

CLAIM: An aromatic liquid bleaching composition containing, as active ingredient, sodium hypochlorite, which comprises one or more of simple perfumes or compounded perfumes selected from the group consisting of anisole, benzophenone, benzylphenyl ether, bromelia, cedrenyl acetate, p-tertiary butylcyclohexanol, dimethylbenzylcarbinyl acetate, dihydroterpinyl acetate, diphenyl oxide, dimethylbenzylcarbinol, dimethylphenylcarbinol, dihydroterpineol, fenchyl acetate, fenchyl alcohol, p-methyldimethylbenzylcarbinol, methylphenylcarbinyl acetate, methyl-n-valerate, muskmoskene, muscarone, methylamyl ketone, phenylethyldimethylcarbinyl acetate, rose phenone, styrallyl propionate, tetra hydromuguol, tetrahydromuguyl acetate, tetrahydrolinalool, tetrahydrolinalyl acetate, verool, velveton, verdox, coniferan and yarayara, and a surface active agent which can stably be dissolved in an aqueous solution of sodium hypochlorite.

Furthermore, the use of such compounds as those having the structure:

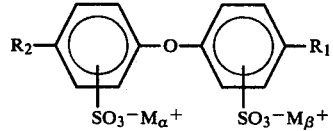

(wherein $R_1$, $R_2$, $M_\alpha$ and $M_\beta$ have been previously defined) with hypochlorite bleaches is documented in the brochure of Dow Chemical entitled "DOWFAX Surfactants" and is covered in the Dow Chemical Company U.S. Pat. No. 3,172,861 issued on Mar. 9, 1965.

Nothing in the prior art discloses, however, the utility of the thickeners of the instant application taken together with a perfume oil (e.g., "diisoamylene" or "diisoamylene epoxide") and one of the compounds defined according to the generic structure:

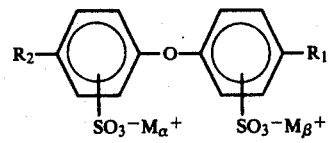

(wherein $R_1$, $R_2$, $M_\alpha$ and $M_\beta$ have been defined, supra) in hypochlorite bleaches, particularly where the hypochlorite concentration is greater than 7%. More particularly, nothing in the prior art discloses the use of such systems in conjunction with a thickener such as sodium palmitate, potassium palmitate, sodium stearate, potassium stearate, sodium laurate, potassium laurate lithium laurate, lithium stearate or lithium palmitate, whereby a stable gelled perfumed hypochlorite mixture is formed or whereby a "premix" gel-phase perfume oil-stabilizing/emulsifying agent is formed.

The 2-methyl-2-octanol of our invention is unique insofar as the aforementioned systems are concerned for use in hypochorite bleaches. Nothing in the prior art discloses any organic compound even remotely similar to 2-methyl-2-octanol for use as a stable aroma augmenting or enhancing agent in hypochlorite bleaches.

Although 2-methyl-2-octanol has heretofore been unknown for use in perfumery, an isomer thereof, 2,6-dimethyl hepanol otherwise known as "lolitol" is well known in the perfume industry and has been used for a number of years in that industry for augmenting or enhancing the aroma of perfumes. However, "lolitol" having the structure:

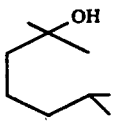

has not been known to be stable in hypochlorite bleaches.

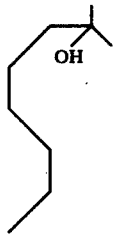

FIG. 4 is the infra-red spectrum for Fraction 4 of the distillation product of the reaction product of Example I containing the compound having the structure:

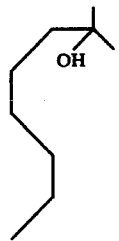

FIG. 5A represents a graph of percent residual chlorine versus time in hours for hypochlorite solutions containing either (i) DOWFAX® 2A1 (a registered trademark of the Dow Chemical Company of Midland, Mich.) identifying a mixture of compounds defined according to the structure:

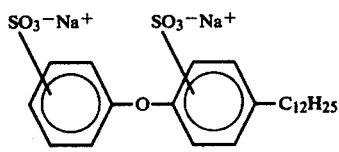

(wherein the $C_{12}H_{25}$ moity is branched chain and the $SO_3-N_a^+$ moieties are at various positions on the benzene ring) or (ii) AROMOX® DMMC-W, a 30% aqueous solution of dimethylcocoamine oxide having the structure:

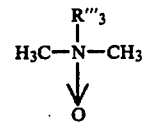

(wherein $R_3'''$ is defined infra) a trademark of Akzo Corporation of Chicago, Ill. (product produced by Armac, Division of Akzo Corporation of Chicago, Ill.) with the weight ratio of AROMOX® DMMC-W:base being 0.8:99 and the ratio of DOWFAX® 2A1:base being 0.8:99, as described in Example XII, infra.

Figure 5B:
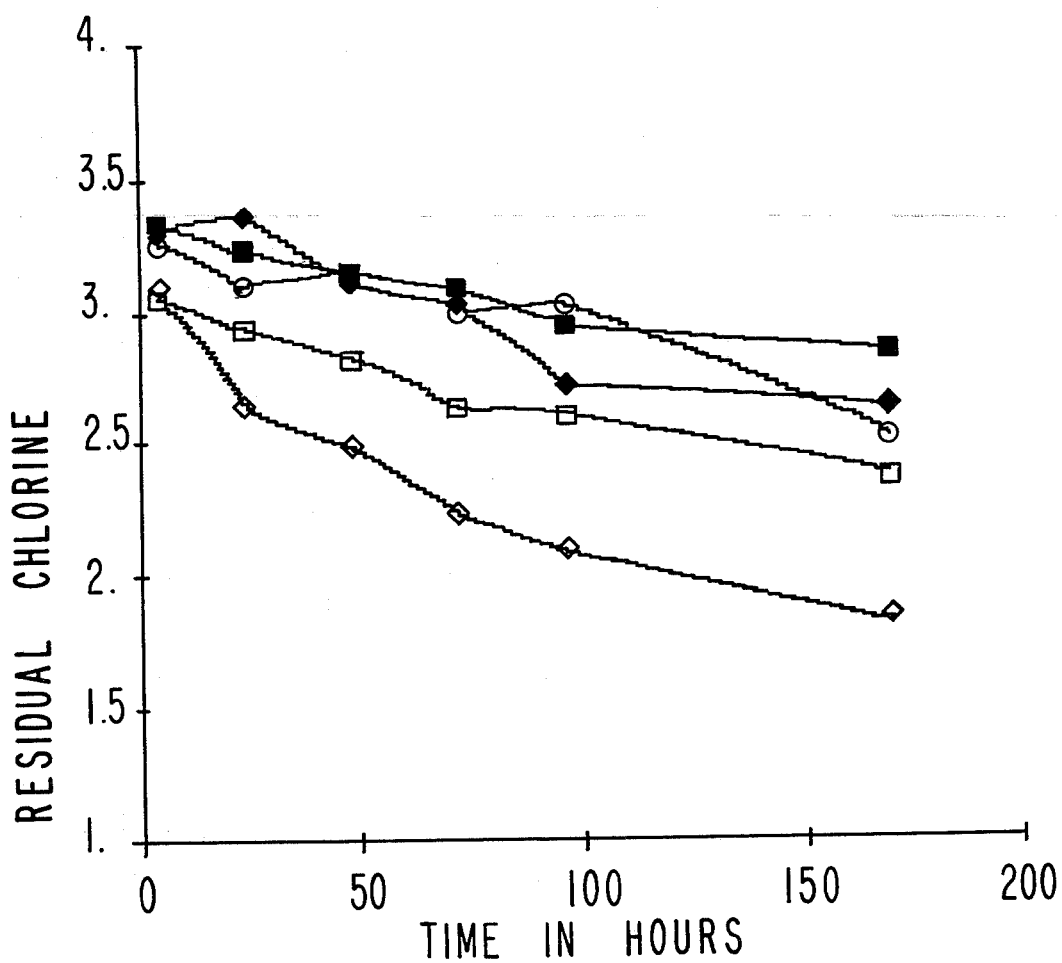

FIG. 5B is a graph of percent residual chlorine versus time in hours for hypochlorite solutions of either (i) DOWFAX® or (ii) AROMOX® DMMC-W, in the absence of fragrance or essential oils with the weight ratio of AROMOX® DMMC-W:base being 1.8:99 and 3.8:96 and the ratios of DOWFAX® 2A1:base being 1.8:99 and 3.8:99, as described in Example XII.

Figure 6A:
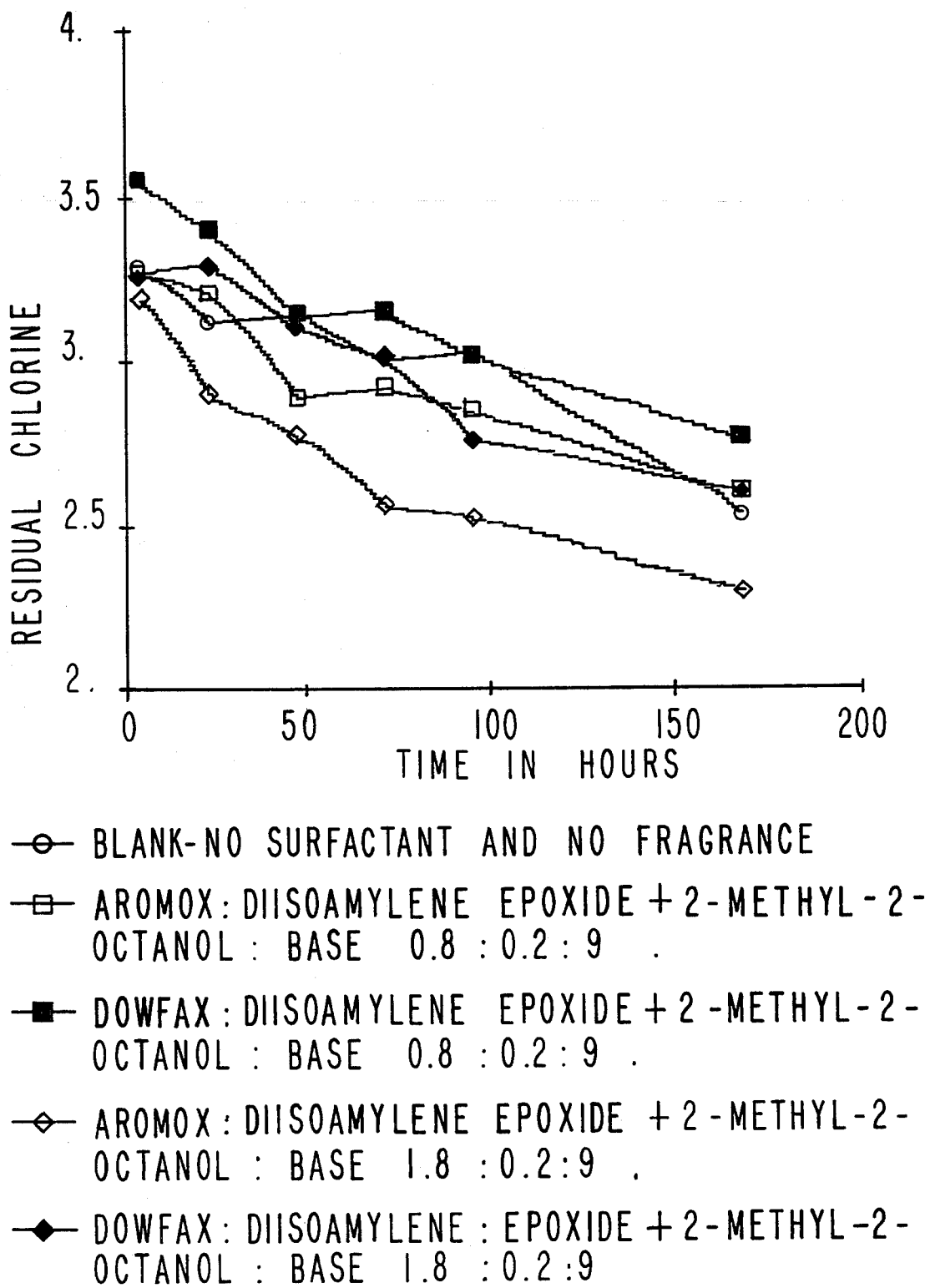

FIG. 6A is a graph of percent residual chlorine versus time in hours comparing the hypochlorite solutions of DOWFAX® 2A1 versus (ii) AROMOX® DMMC-W, with a perfuming material which is a 50:50 mixture of diisoamylene epoxide produced according to Example II of application for U.S. Ser. No. 277,131 filed on June 25, 1981 and 2-methyl-2-octanol, wherein the weight ratio of AROMOX® DMMC-W:mixture of diisoamylene epoxide and 2-methyl-2-octanol:base is either 0.8:0.2:9 or 1.8:0.2:9 and the weight ratio of DOWFAX®:mixture of diisoamylene epoxide and 2-methyl-2-octanol:base is 0.8:0.2:9 or 1.8:0.2:9, as described in Example XII, infra.

Figure 6B:
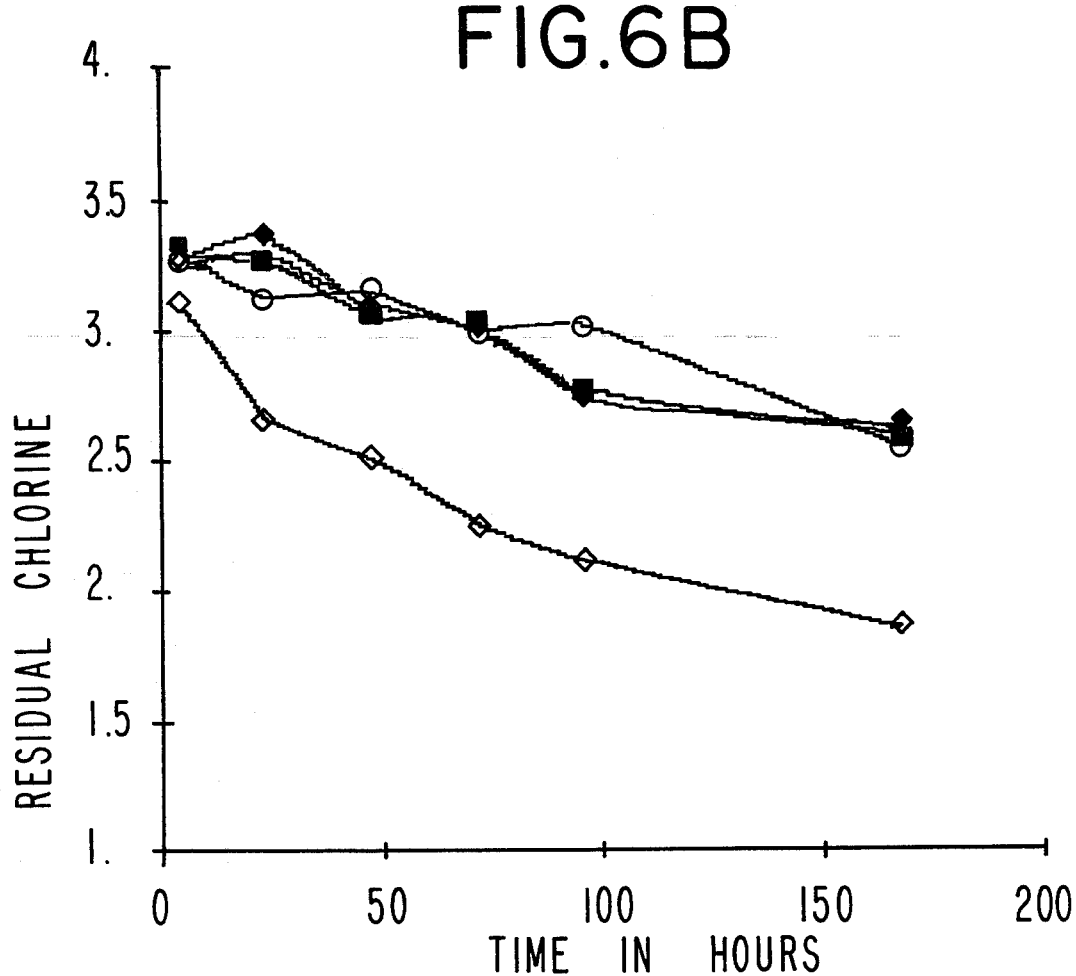

FIG. 6B is a graph of percent residual chlorine versus time in hours comparing the performance of hypochlorite solutions of (i) DOWFAX® 2A1 versus (ii) ARO- MOX ® DMMC-W using a 50:50 mixture of diisoamylene epoxide produced according to Example II of application for U.S. Ser. No. 277,131 filed on June 25, 1981 and 2-methyl-2-octanol with the weight ratio of AROMOX ® DMMC:W:mixture of diisoamylene epoxide and 2-methyl-2-octanol:base being 3.8:0.2:9 and the weight ratio of DOWFAX ® 2A1:mixture of diisoamylene epoxide and 2-methyl-2-octanol:base being 3.8:0.2:9 as described in Example XII, infra.

THE INVENTION

This invention relates to the production of both thickened, highly viscous (20–60 centipoises at 20°–40° C.) perfumed single phase aqueous alkali metal hypochlorite solutions and perfumed single phase aqueous alkali metal hypochlorite solutions which have a low viscosity (5–20 centipoises at 20°–40° C.), having excellent surface tension characteristics and being suitable for laundry and general domestic bleaching and sterilizing purposes. We have now found that it is possible to provide perfumed aqueous alkali metal hypochlorite solutions containing 2-methyl-2-octanol having the structure:

which yield a long lasting perfume aroma (e.g., powerful, citrus [lime] pear like, sweet, floral-fruity, bergamot-like aroma) and which are capable of imparting to surfaces (e.g., laundry and the hands of the user which are in direct contact with the hypochlorite solutions) to which they are applied a pleasant aroma and at the same time substantially diminishing or eliminating altogether the characteristic disagreeable "hypochlorite" aroma therefrom.

Accordingly, this invention consists of an aqueous (i) thickened, highly viscous (20–60 centipoises at 20°–40° C.) solution and (ii) non-viscous (5–20 centipoises at 20°–40° C.) solution of at least one alkali metal hypochlorite containing a stable perfume oil which consists of 2-methyl-2-octanol, optionally a $C_{10}$–$C_{20}$ alkanoic acid alkali metal salt thickener and a surface active agent either consisting (i) solely of a $C_{10}$–$C_{12}$ alkyl diphenyl oxide dialkali metal sulfonate having the structure:

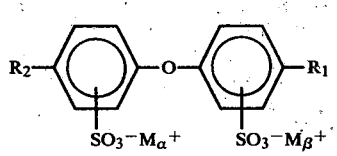

wherein at least of $R_1$ or $R_2$ is straight chain or branched chain $C_{10}$–$C_{12}$ alkyl and when one of $R_1$ or $R_2$ is straight chain or branched chain $C_{10}$–$C_{12}$ alkyl the other of $R_1$ or $R_2$ is hydrogen and wherein $M_\alpha$ and $M_\beta$ are the same or different and each is an alkali metal such as sodium, potassium or lithium; for example the compounds defined according to the structure:

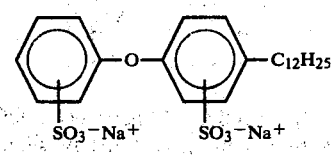

(wherein $C_{12}H_{25}$ represents several $C_{12}$ branched chain moieties) or the compounds defined according to the structure:

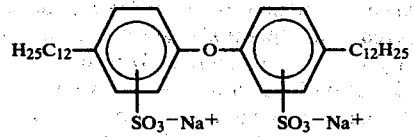

(wherein $C_{12}H_{25}$ represents several $C_{12}$ branched chain moieties) or the compounds defined according to the structure:

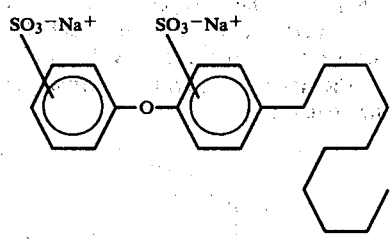

or the compounds defined according to the structure:

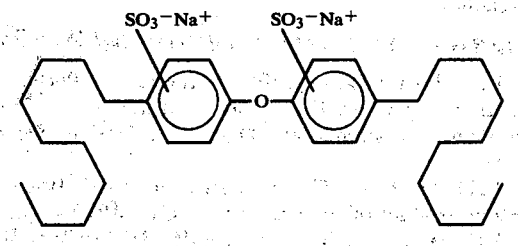

or mixtures of one or more of the foregoing compounds, or (ii) a mixture of at least one compound defined according to the generic structure:

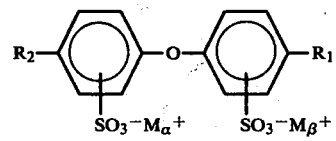

(wherein $R_1$, $R_2$, $M_\alpha$ and $M_\beta'$ are defined supra) and an amine oxide composition consisting essentially of one or more morpholine and/or dimethyl $C_{11}$–$C_{13}$ straight chain alkyl amine oxide having the generic structure:

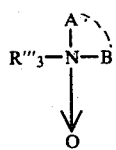

in an amount greater than 55% of said amine oxide composition wherein $R_3'''$ is straight chain alkyl having from 11 up to 13 carbon atoms and A and B are each separately methyl, or taken together, complete a morpholino ring and having a pH in the range of 11–14.0.

The chain lengths of the $R_3'''$ moiety (or moieties) of the predominating alkyl dimethyl amine oxides of the amine oxide composition aids in providing for an aqueous hypochlorite bleach or sterilizing solution which can be perfumed (e.g., in the citrusy sweet, floral-fruity, pear like and bergamot aroma) formulations required for our invention, but the compound having the structure:

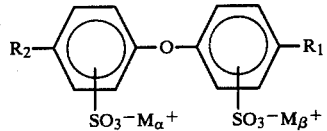

or mixture of such compounds taken alone or taken further together with the alkyl dimethyl amine oxide composition will aid even further in providing such a highly viscous perfumed hypochlorite bleach formulation and the compounds defined according to the structure:

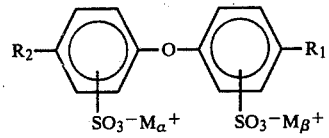

as stated above may be used alone.

The concentration of the composition of matter consisting essentially of the compounds having the structure:

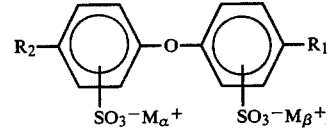

(wherein $R_1$, $R_2$, $M_\alpha$ and $M_\beta$ are defined supra) taken alone or taken in admixture with the amine oxide composition required to create the transparent liquid phase or gel phase solution of this invention is from 0.10% up to 2.0% based on the total weight of solution. Concentrations of diphenyl oxide derivatives less than 0.10% or mixtures of diphenyl oxide derivatives and amine oxides of less than 0.10% will not give rise to the desired single liquid or gel phase system containing the desired special perfume oil consisting essentially of one or more diisoamylene epoxide isomers having an aroma profile required for this invention. From a commercial standpoint the concentration of $C_{10}$–$C_{12}$ straight chain or branched chain alkyl substituted diphenyl oxide dialkali metal sulfonate (hereinafter referred to as "diphenyl oxide derivatives") taken alone or taken in conjunction with amine oxide greater than 2.0% based on the total weight of hypochlorite solution are not needed and give rise to unnecessary costs.

The pH range of the aqueous alkali metal hypochlorite solution containing the $C_{10}$–$C_{12}$ straight chain or branched chain substituted diphenyl oxide dialkali metal sulfonate composition having the structure:

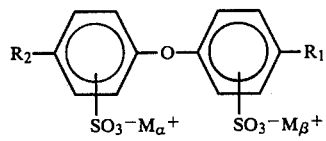

taken alone or in conjunction with the amine oxide composition having the structure:

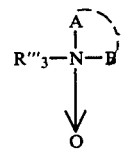

and one of the requisite perfume formulation consisting essentially of one or more of the diisoamylene epoxide derivatives of our invention which are stable to aqueous hypochlorite and which are capable of yielding and imparting the desired and required overall fragrance impression is critical; that is, pH of from 11 up to 14.0 is required for the composition of our invention, with a preferred pH range being between 12.0 and 13.1. The requisite pH range is achieved by adding an aqueous solution of alkali metal hydroxide (e.g., from 1 molar up to 12.5 molar) to the alkali metal hypochlorite solution which has had or will have added to it the $C_{10}$–$C_{12}$ straight or branched chain alkyl substituted diphenyl oxide dialkali metal sulfonate perfume oil premix or the $C_{10}$–$C_{12}$ straight or branched chain alkyl substituted diphenyl oxide dialkali metal sulfonate-amine oxide 2-methyl-2-octanol premix.

The percentage of 2-methyl-2-octanol having the properties yield a pleasant aroma is in the range of from 0.01% up to 0.8% based on the total final weight of alkali metal hypochlorite solution. Lower concentrations of 2-methyl-2-octanol will not be adequate to give rise to the desired substantial diminution or elimination of the characteristic disagreeable hypochlorite aroma (which exists on, for example, laundry and/or the hands of the individual user which have been in direct contact with the hypochlorite bleach or sterilizing solution subsequent to the use of aqueous hypochlorite solutions as a general domestic bleach or sterilizer). Quantities of 2-methyl-2-octanol greater than 0.8% have been found to be uneconomical and unnecessary for the practice of our invention. Useful, optionally, with the 2-methyl-2-octanol in the practice of our invention are the diisoamylene epoxide derivatives of application for U.S. Ser. No. 231,773 filed on Feb. 27, 1981 or the dimethyl epoxide derivatives of application for U.S. Ser. No. 231,773 filed on Feb. 27, 1981 together with (i) diisoamylenes of application for U.S. Ser. No. 188,576 filed on Oct. 9, 1980 or (ii) acyl diisoamylene derivatives described in application for U.S. Ser. No. 184,132 filed on Sept. 4, 1980 and/or ketal derivatives thereof as described in application for U.S. Ser. No. 212,993 filed on Dec. 4, 1980. Not only is the cost of the 2-methyl-2-octanol very low but the very low cost of the diisoamylene epoxide derivatives taken alone or further together with other diisoamylene derivatives as set forth above and the high stability of the 2-methyl-2-octanol and the diisoamylene epoxide derivatives taken alone or together with other diisoamylenes as set forth, supra, gives rise to a very economical use of 2-methyl-2-octanol alone or in admixture even at very high levels.

The 2-methyl-2-octanol of our invention may be produced by either (a) reaction of a methyl grignard reagent such as methyl magnesium chloride with an alkyl ester of n-heptanoic acid to yield a grignard salt which can be hydrolized to the 2-methyl-2-octanol of our invention or (ii) reaction of a methyl grignard reagent such as methyl magnesium chloride with 2-octanone to yield an organo metallic salt which is further reacted with weak acid to produce the 2-methyl-2-octanol of our invention. Thus, generically the reactions are as follows (a):

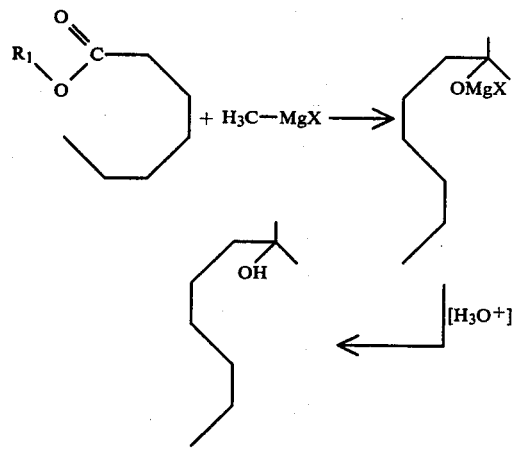

wherein $R_1$ is lower alkyl, conveniently and economically methyl or ethyl and wherein X is halogen, conveniently chloro or bromo and where the acid used in the hydrolysis is a weak acid such as dilute (0.1 molar) hydrochloric acid or (0.5-1 molar) acetic acid or (b) the reaction:

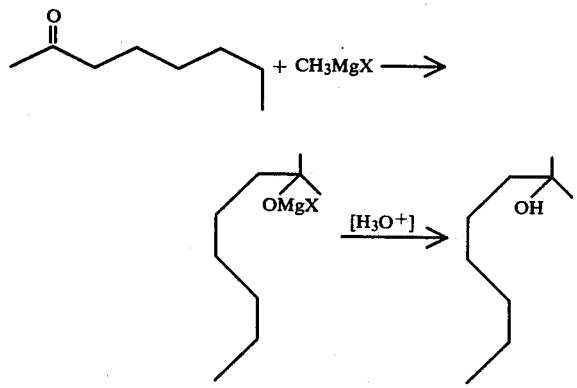

wherein X is halogen, conveniently chloro or bromo and the acid hydrolysis takes place using a dilute acid such as acetic acid, dilute hydrochloric acid or ammonium chloride in aqueous solution.

More specifically, ethyl-n-heptanoate may be reacted with methyl magnesium chloride to form the organo metallic intermediate having the structure:

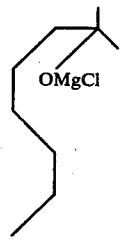

according to the reaction:

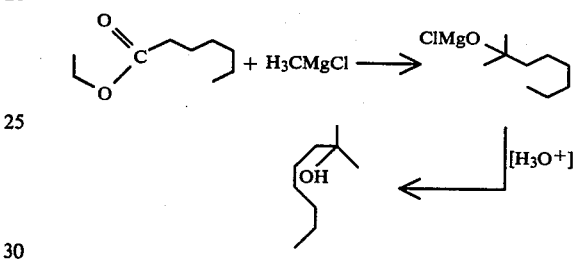

wherein the organo metallic compound is hydrolyzed using dilute acid in accordance with, for example, the procedure of Example I.

In carrying out the reaction between methyl magnesium halide and the alkyl-n-heptanoic acid ester, methyl magnesium chloride or methyl magnesium bromide may be used and it is preferable to use the ethyl or methyl esters. The mole ratio is preferably from 2.5 moles methyl magnesium halide; 1 mole alkyl-n-heptanoate down to 2 moles methyl magnesium halide; 1 mole ethyl-n-heptanoate or alkyl heptanoate. The reaction temperature is at reflux, conveniently, at atmospheric pressure or at pressures greater than atmospheric. At atmospheric pressure the reaction temperature may vary between 55° and 65° C., depending upon the particular ester utilized for the reaction. Thus, for example, when the ethyl ester of n-heptanoic acid is used the reaction temperature is 61° C. at atmospheric pressure. The hydrolysis reaction may take place using dilute hydrochloric acid or acetic acid, for example, at concentrations of between 10% and 50%, preferably 25% acetic acid. Alternatively, the hydrolysis reaction may take place using between 0.5 m and 2 m ammonium chloride. At the end of the hydrolysis reaction the reaction product, the 2-methyl-2-octanol is distilled at a vapor temperature of 68° C. at between 8 and 10 mm Hg vacuum.

Several processes may be used in order to produce a thickened, highly viscous hypochlorite bleaching or sterilizing solution whereby the desired aroma profiles are imparted to the articles treated with said hypochlorite solutions. Thus, for example, 2-methyl-2-octanol may be premixed with the diphenyl oxide derivative or diphenyl oxide derivative-amine oxide solubilizer-stabilizer (having the structures, respectively:

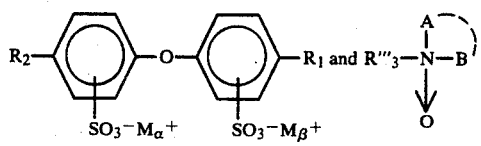

and the resulting 2-methyl-2-octanol-diphenyl oxide derivative or 2-methyl-2-octanol-diphenyl oxide derivative-amine oxide premix is then mixed with the hypochlorite bleaching or sterilizing solution with stirring. Immediately after such addition, an aqueous alkali metal hydroxide solution is added to the mixture to bring the pH to the range of 11–14.0. A pH of less than 11 is not desired since it is difficult to achieve a single phase stable system at low pH's. A pH higher than 14.0 will also create a system which (1) is unnecessarily corrosive; (2) will narrow the range of perfume oils useable (in conjunction with the 2-methyl-2-octanol) of the system and (3) will limit the particular ingredients useable in such perfume oils in conjunction with the 2-methyl-2-octanol. On the other hand, if for example, the 2-methyl-2-octanol is used alone or further in combination with (i) diisoamylene epoxides; (ii) diisoamylenes as described in application for U.S. Ser. No. 188,576 filed on Oct. 9, 1980; or (iii) acyl diisoamylene derivatives described in application for U.S. Ser. No. 184,132 filed on Sept. 4, 1980 and/or (iv) ketal derivatives of acyl diisoamylene derivatives described in application for U.S. Ser. No. 212,993 filed on Dec. 4, 1980, a pH of about 14.0 and even slightly higher (e.g., 14.1) is acceptable.

The aqueous alkali metal hydroxide can be added to the aqueous alkali metal hypochloride solution before adding the diphenyl oxide derivatives (taken alone or in conjunction with the amine oxide) or the 2-methyl-2-octanol or mixtures of 2-methyl-2-octanol with other materials such as diisoamylene epoxides. Indeed, the ingredients: the 2-methyl-2-octanol; the alkali metal hydroxide and the diphenyl oxide derivative or diphenyl oxide derivative-amine oxide composition (having the structures respectively):

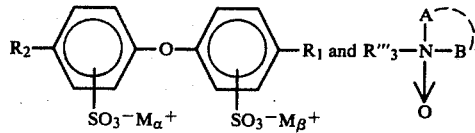

may be added or admixed in any order which is convenient to the formulator. One desirable process involves first forming the diphenyl oxide derivative or diphenyl oxide derivative-amine oxide composition-2-methyl-2-octanol "premix", mixing the premix with the alkali metal hypochlorite solution and finally adjusting the pH of the solution with alkali metal hydroxide to bring the pH to within the range of 11–14.0. A second, more preferable process, involves first adjusting the pH of the aqueous alkali metal hypochlorite solution to 11–14.0 and then admixing the solution with the afore-described "premix".

The alkali metal hypochlorites preferred in the practice of our invention are: sodium hypochlorite, potassium hypochlorite and lithium hypochlorite or mixtures of same. The alkali metal hydroxides preferred in the practice of this invention are: lithium hydroxide, potassium hydroxide and sodium hydroxide or, if desired, mixtures of such hydroxides.

The temperature at which the composition of our invention remains both substantially stable and commercially useful for the purposes set forth herein (that is, remains as a clear single aqueous or gel phase and retains (1) the desired properties inherent in the known bleaching and sterilizing uses of aqueous alkali metal hypochlorite liquid or gel solutions, and (2) the properties imparted thereto as a result of use of the 2-methyl-2-octanol which impart to articles previously subjected to the aqueous alkali metal hypochlorite gel or liquid solutions a desired aroma profile, varies from approximately 20° F. up to approximately 120° F. At temperatures below 20° F. a two-phase system usually occurs and at temperatures higher than 120° F. the bleaching or sterilizing efficiency of the compositions of our invention is diminished at an excessive rate.

When it is desired to (1) initially form the $C_{10}$-$C_{12}$ straight chain or branched chain diphenyl oxide alkali metal sulfonate or diphenyl oxide derivative-amine oxide-2-methyl-2-octanol premix; (2) then combine the resulting premix with an aqueous alkali metal hypochlorite solution; (3) then add the thickening agent and then (4) adjust the pH of the resulting solution to the range of 11–14.0, then the temperature of mixing ranges are considered to be within the scope of this invention as follows:

| | |
|---|---|
| (a) Formation of the diphenyl oxide derivative or diphenyl oxide-amine oxide - 2-methyl-2-octanol premix | 20° F.–150° F. |
| (b) Mixing the premix with aqueous metal alkali hypochlorite solution followed by thickening agent | 20° F.–120° F. |
| (c) Adjustment of pH of the solution to the range of 11–14.0 using aqueous alkali metal hydroxide solution | 20° F.–120° F. |

In any event, wherever a mixing unit operation involves the aqueous alkali metal hypochlorite solution, the temperature of mixing is limited to the range of 20° F.–120° F. Where the mixing unit operation involves the mixing of 2-methyl-2-octanol, the upper bound of the temperature range is limited by the stability of the 2-methyl-2-octanol or other perfume ingredient mixed with the 2-methyl-2-octanol useable in the practice of our invention; and the lower bound of said temperature range is limited by the least temperature where a single liquid phase or gel phase including the 2-methyl-2-octanol or other ingredient admixed therewith will exist. Where a unit mixing operation of the process of our invention involves the mixing of one or more diphenyl oxide derivatives having the generic structure:

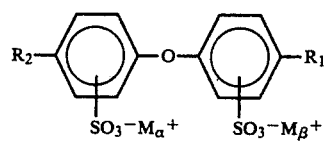

taken alone or taken together with one or more amine oxides having the generic structure:

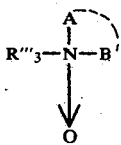

with other materials, the upper bound of the temperature range is the decomposition point of any one of the diphenyl oxide derivatives or amine oxide components and the lower bound is the least temperature where a single liquid phase or gel phase, including the diphenyl oxide derivatives or diphenyl oxide-amine oxide mixture will exist.

Preferred diphenyl oxide derivative compositions from a practical standpoint useful in the practice of our invention are compounds having the structure:

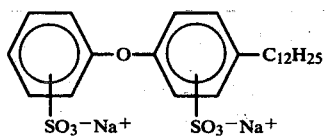

where the $C_{12}H_{25}$ moiety represents one or a series of different branched chains; compounds defined according to the structure:

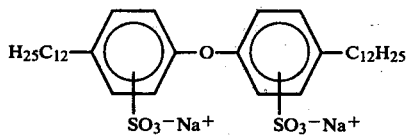

where the $C_{12}H_{25}$ moiety represents one or a series of different branched chains; compounds defined according to the structure:

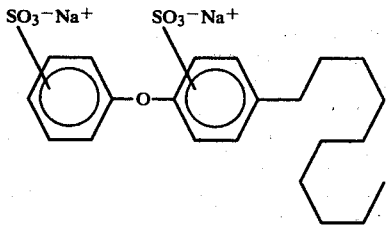

and compounds defined according to the structure:

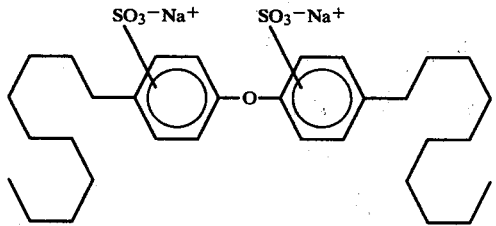

otherwise known as DOWFAX® 2A1 in the case where one of $R_1$ or $R_2$ represents branched $C_{12}H_{25}$ alkyl chains and the other of $R_1$ or $R_2$ represents hydrogen, or DOWFAX® 3B2 in the case where one of $R_1$ or $R_2$ represents straight $C_{10}$ alkyl chain and the other of $R_1$ or $R_2$ represents hydrogen (DOWFAX® being a registered trademark of the Dow Chemical Company of Midland, Mich.).

When used in conjunction with the diphenyl oxide derivatives preferred amine oxide compositions, from a practical standpoint, useful in the practice of our invention are the commercially available (1) dimethyl "cocoamine" oxide (a mixture which is dominated by dimethyl-$C_{12}$-$C_{16}$ straight chain alkyl amine oxides; more particularly a mixture containing approximately 70% $C_{12}$ straight chain alkyl amine oxides, approximately 25% of straight chain $C_{14}$ alkyl amine oxides and approximately 4% straight chain $C_{16}$ alkyl amine oxides) and (2) N-cocomorpholine oxide, a mixture dominated by straight chain $C_{12}$-$C_{16}$ alkyl morpholine oxides (specifically containing approximately 70% straight chain $C_{12}$ alkyl morpholine oxide, approximately 25% straight chain $C_{14}$ alkyl morpholine oxide, and approximately 4% straight chain $C_{16}$ alkyl morpholine oxide). Commercial examples of such amine oxide compositions are: Aromox® DMC-W and Aromox® DMMC-W which are 30% aqueous dimethyl cocoamine oxide solutions and Aromox® NCMDW which is a 40% aqueous N-cocomorpholine oxide solution, each of which is produced by the Armac Division of AKZO of Chicago, Ill. These materials are described in Brochure 68011, published by Armour Industrial Chemicals, P.O.B. 1805, Chicago, Ill. 60690. Other preferred amine oxides are n-undecyl dimethyl amine oxide and n-tridecyl dimethyl amine oxide.

The percentage of hypochlorite ion in the compositions of our invention may vary from about 1% up to about 20% for the desired effects to be produced using the diphenyl oxide derivative or diphenyl oxide derivative-amine-oxide 2-methyl-2-octanol compositions covered by our invention. The usual percent of alkali metal hypochlorite in solution is about 5%, the percentage of sodium hypochlorite in such mixtures as CLOROX® the registered trademark of the Clorox Corporation.

The perfume oil used in conjunction with the 2-methyl-2-octanol which in turn, is used in conjunction with the aqueous alkali metal hypochlorite solution must have such properties as to be able (1) to be compatible with the 2-methyl-2-octanol of our invention; (2) to impart to the resulting or "aqueous alkali metal hypochlorite" liquid or gel solution a pleasant aroma which harmonizes with the aroma of the 2-methyl-2-octanol; (3) to effect a substantial diminution or elimination of the disagreeable "hypochlorite" aroma which is imparted to surfaces (e.g., bleached laundry or the hands of the user which are in direct contact with the hypochlorite solution) on which known aqueous alkali metal hypochlorite solutions have been used; and (4) to impart to the surfaces with which such aqueous alkali metal hypochlorite solutions are in contact, a pleasant long lasting stable aroma. Examples of ingredients compatible with 2-methyl-2-octanol and suitable for the aforementioned purposes, that is, usable in conjunction with the hypochlorites, amine oxide derivatives and diphenyl oxide derivatives of our invention are as follows:

1. Cedryl alkyl ethers covered by U.S. Pat. No. 3,373,208 such as cedryl methyl ether;
2. Isochroman musks covered by U.S. Pat. No. 3,360,530 and 3,591,528 such as 6-oxa-1,1,3,3,8-pentamethyl-2,3,5,6,7,8-hexahydro-1H-benz(f)indene;

3. Polycyclic ethers covered by U.S. Pat. No. 3,281,432, such as octahydro-1,3a,6-trimethyl-1H-1,6a,ethanopentaleno-(1,2-C)furan;

4. Polycyclic ketones such as hexahydro-1,1,5,5-tetramethyl-2H-2,4a-methanonaphthalen-8-(5H)one.

5. Diisoamylenes described according to application for U.S. Ser. No. 188,576 filed on Sept. 18, 1980;

6. Acyl diisoamylene derivatives described according to application for U.S. Ser. No. 184,132 filed on Sept. 4, 1980 and ketal derivatives thereof described according to application for U.S. Ser. No. 212,993 filed on Dec. 4, 1980.

7. Diisoamylene epoxide derivatives prepared according to application for U.S. Ser. No. 231,773 filed on Feb. 27, 1981.

It will be understood that a number of materials which impart to the citrusy floral aroma of 2-methyl-2-octanol of our invention additional eucalyptol-like, or minty or woody nuances will not be useful for our invention because they are, interalia, easily oxidized by the alkali metal hypochlorite in the system. Examples are 1,5,9-trimethyl-12-acetyl-cyclododecatriene-1,5,8 and 1,5,9-trimethyl-12-cyclodecadiene-1,8 covered by British Pat. No. 1,204,409.

A basic feature of our invention concerns the fact that the only detergent group needed or desirable in the composition of our invention is the class of diphenyl oxide derivatives defined according to the structure:

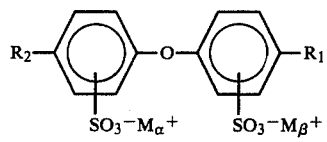

wherein $R_1$, $R_2$, $M_\alpha$ and $M_\beta$ are defined, supra, taken alone or in conjunction with the class of morpholino and/or dimethyl $C_{11}$–$C_{13}$ straight chain alkyl amine oxides defined according to the structure:

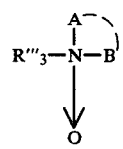

More specifically, such detergents as sodium decyl ether sulfate, sodium myristyl ether sulfate, sodium lauryl ether sulfate and lithium lauryl ether sulfate are neither desired nor are they required. Furthermore the well known hydrotropes employed in prior art compositions such as the well known family of clarifying agents comprising the alkali metal or alkali earth metal salts of mono- and polyalkylated benzene or naphthalene sulfonates such as sodium xylene or magnasium toluene sulfonate are again neither desired nor are they required in the compositions intended to be encompassed by the instant invention.

Another basic feature of our invention concerns the fact that when it is desired to have a gel phase composition, thickener agents may be employed in conjunction with the system; hypochlorite bleach-2-methyl-2-octanol-diphenyl oxide derivative or diphen oxide-derivative-amine oxide derivative (having the general structure):

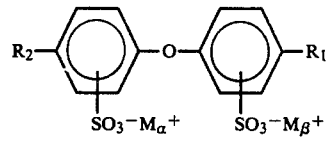

and having the structure:

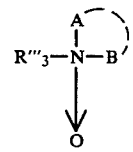

of our invention.

Still another basic feature of our invention concerns the fact that the gel phase compositions including thickener agents are employed with the "premix" system: 2-methyl-2-octanoldiphenyl oxide derivative or diphenyl oxide derivative-amine oxide of our invention.

Thus, sodium palmitate, sodium stearate, sodium laurate, potassium palmitate, potassium stearate, potassium laurate, lithium palmitate, lithium stearate and/or lithium laurate or combinations of the foregoing may be added to the compositions of matter of our invention to provide a thickened gel-type hypochlorite bleach which is, in addition to being a semi-solid state, is unobviously, advantageously and unexpectedly stable over long periods of time. Percentages of thickening agents such as sodium palmitate, sodium stearate, sodium laurate, potassium palmitate, potassium stearate, potassium laurate, lithium palmitate, lithium stearate or lithium laurate or combinations of these which may be used in the thickened compositions of our invention are from 1% by weight up to 12% by weight of the thickener based on the overall weight of hypochlorite bleach-diphenyl oxide derivative (or diphenyl oxide derivative-amine oxide)-2-methyl-2-octanol composition of our invention. When it is merely desired to have a thickened "premix" the percentage of thickening agent may vary from about 5% up to about 40% by weight of thickener based on overall weight of "premix".

The following examples are given to illustrate embodiments of the invention as it is now preferred to practice it. It will be understood that these examples are illustrative and the invention is not to be considered as restricted thereto except as indicated in the appended claims.

EXAMPLE I

Preparation of 2-Methyl-2-octanol

Reaction:

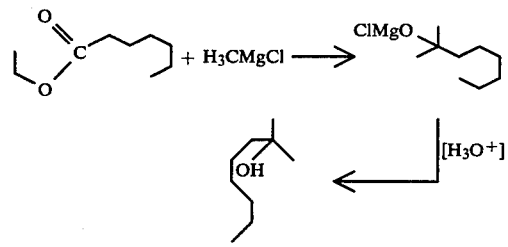

into a 3000 ml reaction flask, equipped with heating mantle stirrer, reflux condenser, thermometer, addition funnel and nitrogen blanket is placed 6.0 moles of methyl magnesium chloride in 2 liters of tetrohydrofuran. This solution is heated to reflux and, while refluxing at 61° C. over a period of two hours is added 474 grams (3.0 moles) of ethyl heptanoate. At the end of the addition the compound having the structure:

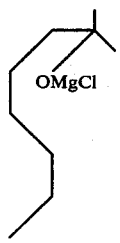

500 cc of 15% HCL is then added to the reaction mixture and the reaction mixture is heated for ten hours. The reaction mass is then transferred to a flask containing 1500 ml of 25% acetic acid.

The reaction mass now exists in two phases, an aqueous phase and an organic phase. The organic phase is separated from the aqueous phase and the organic phase is washed neutral with a sodium chloride solution and stripped of tetrahydrofuran. The reaction mass is then distilled yielding the following fractions:

| Fraction No. | Vapor Temp. | Liquid Temp. | Head Vacuum mm. | Reflux Ratio | Weight Fraction |
|---|---|---|---|---|---|
| 1 | 55/57 | 75/75 | 6/9 | 4:1 | 78 |
| 2 | 68 | 82 | 9.0 | 4:1/9:1 | 82 |
| 3 | 68 | 82 | 8.5 | 9:1 | 61 |
| 4 | 68 | 98 | 9.0 | 9:1 | 74 |
| 5 | 131 | 210 | 9.0 | 9:1 | 52 |

Figure 1:
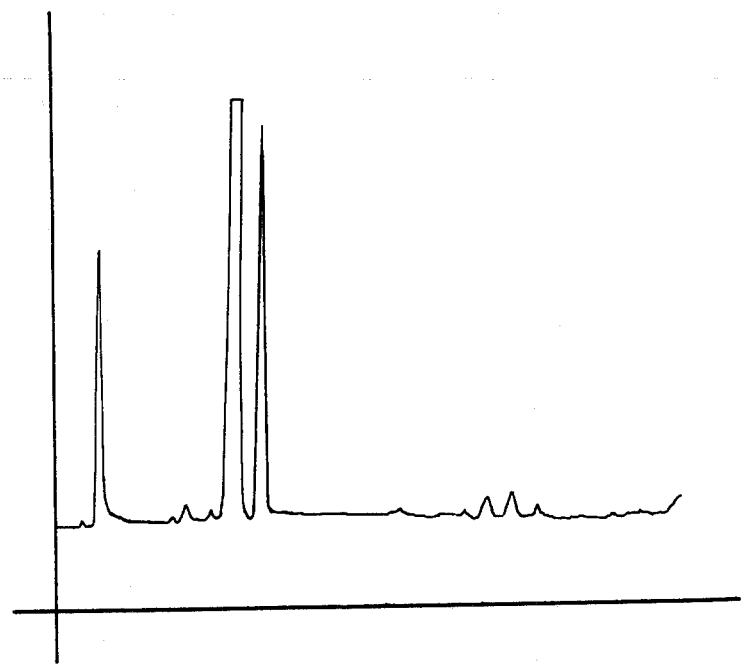
FIG. 1 is the GLC profile for the reaction product of Example I prior to distillation (conditions: 6'×⅛" SE-30 column programmed at 100°–220° C. at 8° C. per minute).

FIG. 1 is the GLC profile for the reaction product prior to distillation (conditions: 6'×⅛" SE-30 column programmed at 100°–220° C. at 8° C. per minute).

Figure 2:
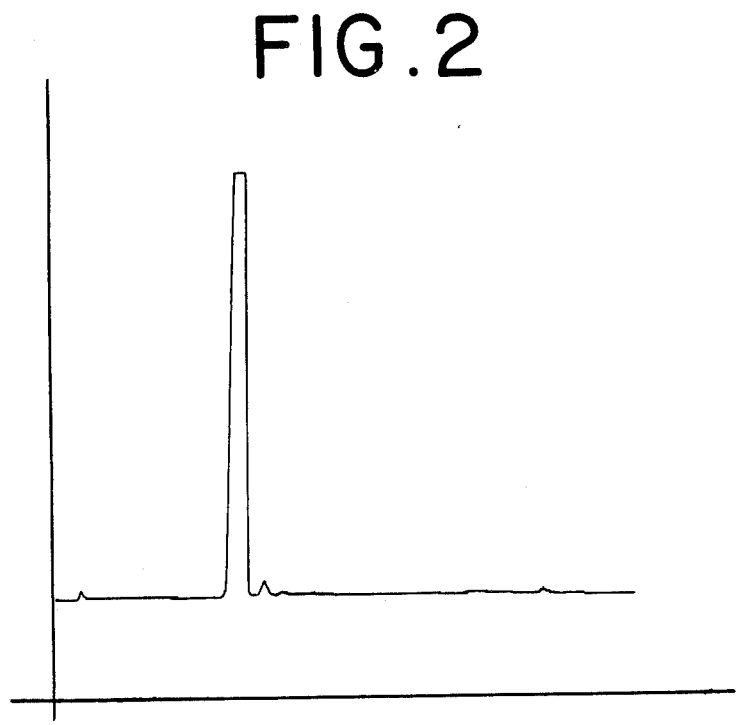
FIG. 2 is the GLC profile for Fraction 4 of the distillation product of the reaction product of Example I.

FIG. 2 is the GLC profile for Fraction 4 of the foregoing distillation.

Figure 3:
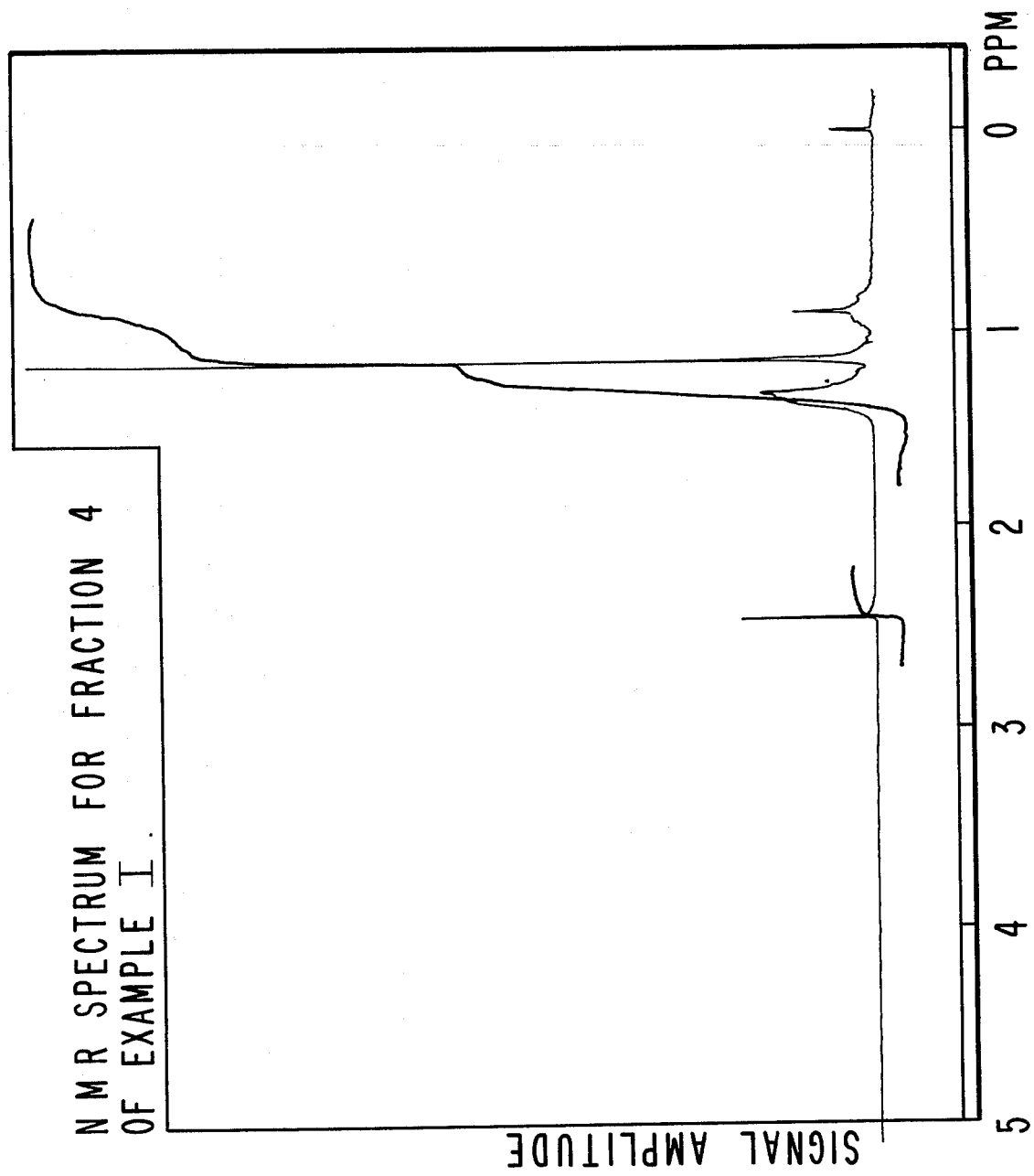
FIG. 3 is the NMR spectrum for Fraction 4 of the distillation product of the reaction product of Example I containing the compound having the structure.

FIG. 3 is the NMR spectrum for Fraction 4 of the foregoing distillation.

FIG. 4 is the infra-red spectrum for Fraction 4 of the foregoing distillation.

In the following examples, Aromox ® DMC-W and Aromox ® DMMC-W are 30% aqueous solutions of dimethyl cocoamine oxide; and Aromox ® NCMDW is a 40% aqueous solution of N-cocomorpholine oxide produced by Armac Division of AKZO of Chicago, Ill.

EXAMPLE II

Four drops of the 2-methyl-2-octanol prepared according to Example I is added to 2 grams of Aromox ® DMC-W to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a faint, pleasant "floral, citrusy" aroma. Furthermore, no such characteristic "hypochlorite" aroma is retained on the hands of the individual handling such laundry in both the wet and the dry states.

EXAMPLE III

Aromox ® DMMC-W in various quantities is mixed with 0.1 grams of 2-methyl-2-octanol prepared according to Example I. The resulting premixes is then added to 200 grams of an aqueous 5% sodium hypochlorite solution. Sufficient 12.5 M aqueous NaOH is added to bring the pH of the mixture up to 13. The following results are obtained:

| Percentage Aromox DMMC-W | Clarity of hypochlorite solution after addition of premix |
|---|---|
| 0.23% | Clear after three days |
| 0.15% | Clear after three days |
| 0.08% | Initially slightly turbid; two phases exist after three days. |

When the 5% aqueous sodium hypochlorite solutions are used as laundry bleaches, the resulting laundry batches on dry-out in an atmosphere of 65% relative humidity yields substantially no characteristic "hypochlorite" odor, but do have faint, pleasant "floral, citrusy" aromas. Furthermore, no such characteristics "hypochlorite" aroma is retained on the hands of the individual handling such laundry batches in both the wet and the dry states.

EXAMPLE IV

Two grams of Aromox ® DMMC-W are admixed with eight drops of 2-methyl-2-octanol one produced according to Example I. The premix is then added with stirring to 200 grams of a 7% aqueous solution of lithium hypochlorite. Sufficient 3 M aqueous LiOH is added to bring the pH of the solution to 13.4. The mixtures are then heated to 120° F. and maintained at that temperature with stirring for a period of one week. The resulting solution remains clear in a single phase. When used as laundry bleaches, the resulting bleached laundry batches on dry-out in an atmosphere of 50% relative humidity retain a "floral, citrusy" aroma; whereas without the use of the 2-methyl-2-octanol prepared according to Example I, the bleached laundry batches have a faint characteristic disagreeable "hypochlorite" aroma.

EXAMPLE V

Two grams of Aromox ® DMMC-W are admixed with eight drops of the 2-methyl-2-octanol produced according to Example I. The premix is then added with stirring to 200 grams of a mixture containing 4.5% aqueous sodium hypochlorite and 4.5% aqueous lithium hypochlorite. Sufficient 4 M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry batches on dry-out in an atmosphere of 50% relative humidity retain a "floral, citrusy" aroma; whereas without the use of the 2-methyl-2-octanol prepared according to Example I, the bleached laundry batches have faint characteristic disagreeable "hypochlorite" aroma.

EXAMPLE VI

Two grams of Aromox® DMMC-W are admixed with eight drops of either (a) the 2-methyl-2-octanol produced according to Example I; or (b) a 50—50 mixture of 2-methyl-2-octanol one and diisoamylene epoxide produced according to Example II of application for U.S. Ser. No. 277,131 filed on June 25, 1981, the disclosure of which is incorporated herein by reference. These premixes are then added with stirring to 200 grams of a mixture containing 4% aqueous sodium hypochlorite and 4% aqueous lithium hypochlorite. Sufficient 2 M aqueous NaOH is added to bring the pH of the solutions to 13.4. The mixtures are then heated to 110° F. and maintained at that temperature with stirring for a period of two weeks. The resulting solutions remain clear as a single phase when used as laundry bleaches. The resulting bleached laundry batches on dry-out in an atomosphere of 50% relative humidity retain either "floral, citrusy" aromas (when using 2-methyl-2-octanol alone) or retain "floral, citrusy, woody" aromas when using the mixture of the diisoamylene epoxide and 2-methyl-2-octanol prepared according to Example I; whereas without the use of the 2-methyl-2-octanol containing compositions of matter the bleached laundry batches have faint characteristic disagreeable "hypochlorite" aromas.

EXAMPLE VII

Four drops of 2-methyl-2-octanol prepared according to Example I are added to 1.5 grams of Aromox® NCMD-W to produce a clear premix. The clear premix is added to 200 grams of CLOROX® with stirring resulting in a clear stable single phase solution. Sufficient 1 M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a faint "floral, citrusy" aroma. Furthermore, no such characteristic "hypochlorite" aroma is retained on the hands of the individual handling such laundry in both the wet and the dry states.

EXAMPLE VIII

Four drops of 2-methyl-2-octanol produced according to Example I, is added to 1 gram of n-undecyl dimethyl amine oxide to produce a clear premix. The clear premix is added to 200 grams of CLOROX® with stirring resulting in a clear stable single phase solution. Sufficient 1 M aqueous NaOH is added to bring the pH of the mixture to 12.8. The solution remains substantially stable at 120° F. for a period of seven days. When the 5% aqueous sodium hypochlorite solution is used as a laundry bleach the resulting laundry on dry-out in an atmosphere of 65% relative humidity yields substantially no characteristic "hypochlorite" odor but does have a faint pleasant "floral, citrusy" aroma. Furthermore, no such characteristic "hypochlorite" aroma is retained on the hands of the individual handling such laundry in both the wet and the dry states.

EXAMPLE IX

Four drops of the 2-methyl-2-octanol produced according to Example I is added to 1 gram of n-dodecyl dimethyl amine oxide to produce a clear premix. The clear premix is added to 200 grams of CLOROX® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasent "citrusy, floral" aroma. Furthermore, no such characteristic "hypochlorite" aroma is retained on the hands of the individual handling such laundry in both the wet and the dry states.

EXAMPLE X

One gram of n-tridecyl dimethyl amine oxide is admixed with eight drops of a 50:50 mixture of the diisoamylene epoxide prepared according to Example II of application U.S. Ser. No. 277,131 filed on June 25, 1981 and 2-methyl-2-octanol prepared according to Example I, supra. This premix is then added with stirring to 200 grams of a 7% aqueous solution of lithium hypochlorite. Sufficient 3 M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains a "citrusy, floral" aroma with "woody, eucalyptol-like and minty" nuances; whereas without the use of the mixture of diisoamylene epoxide and 2-methyl-2-octanol bleached laundry has a faint characteristic disagreeable "hypochlorite" aroma.

EXAMPLE XI

Aromox® DMMC-W in various quantities is mixed with 0.1 gram of a 25:75 weight:weight mixture of diisoamylene epoxide:2-methyl-2-octanol. The resulting premixes are then added to 200 grams of an aqueous of 5% sodium hypochlorite solution. Sufficient 12.5 M aqueous NaOH is added to bring the pH of the mixture up to 13. The following results are obtained:

| Percentage Aromox® DMMC-W | Clarity of hypochlorite solution after addition of premix |
|---|---|
| 0.23% | Clear after three days |
| 0.15% | Clear after three days |
| 0.08% | Initially slightly turbid; two phases exist after three days. |

When used as laundry bleaches, the resulting bleached laundries on dry-out in an atmosphere of 50% relative humidity in each of the three cases above retain a "citrusy, floral" aroma with "woody, eucalyptol-like and minty" nuances, whereas without the use of the composition of matter set forth above containing diisoamylene epoxide and 2-methyl-2-octanol the bleached laundry has the same characteristic disagreeable "hypochlorite" aroma.

EXAMPLE XII

Dowfax® 2A1 (see Note 1, infra) in various quantities, as set forth below, is mixed with 0.1 grams of a 50:50 mixture of (a) one of the diisoamylene epoxide compositions prepared according to Example II of application for U.S. Ser. No. 277,131 filed on June 25, 1981 and (b) 2-methyl-2-octanol prepared according to Example I. The resulting premixes are then added to 200 grams of an aqueous 7% sodium hypochlorite solution. Sufficient 12.5 M aqueous sodium hydroxide is added to bring the pH of the mixture up to 13.5. The following results are obtained:

| Percentage of DOWFAX® 2A1 | Clarity of hypochlorite solution after addition of premix |
|---|---|
| 0.23% | Clear after seven days |
| 0.15% | Clear after five days |
| 0.08% | Clear after three days |
| 0.01% | Initially slightly turbid; two phases exist after three days. |

FIG. 5A represents a graph of percent residual chlorine versus time in hours for hypochlorite solutions containing DOWFAX® 2A1 (a registered trademark of the Dow Chemical Company of Midland, Mich.) identifying the compound having the structure:

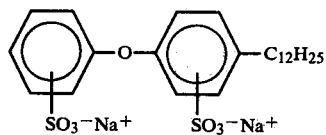

wherein the $C_{12}H_{25}$ moiety is branched chain and the $SO_3-Na+$ moieties are at various positions on each of the benzene rings or AROMOX® DMMC-W, a 30% aqueous solution of dimethylcocoamine oxide having the structure:

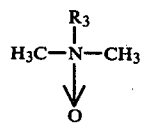

a trademark of Akzo Corporation of Chicago, Ill. (product produced by Armac, Division of Akzo Corporation of Chicago, Ill.) with the ratio of AROMOX® DMMC-W:base being 0.8:99 and the ratio of DOWFAX® 2A1:base being 0.8:99.

FIG. 5B is a graph of percent residual chlorine versus time in hours for hypochlorite solutions of (1) DOWFAX® 2A1 and AROMOX® DMMC-W in the absence of any fragrance or essential oils with the weight ratios of AROMOX® DMMC-W:base being 1.8:99 and 3.8:96 and the weight of ratios of DOWFAX® 2A1:base being 1.8:99 and 3.8:99.

FIG. 6A is a graph of percent residual chlorine versus time in hours comparing hypochlorite solutions of DOWFAX® 2A1 versus AROMOX® DMMC-W with the perfuming material being a 50:50 mixture of one of the diisoamylene products produced according to Example II, of application for U.S. Ser. No. 277,131 filed on June 25, 1981 and 2-methyl-2-octanol produced according to Example I, supra, wherein the weight ratio of AROMOX® DMMC-W:mixture of diisoamylene epoxide and 2-methyl-2-octanol:base being either 0.8:0.2:9 or 1.8:0.2:9 and the weight ratio of DOWFAX® 2A1:mixture of diisoamylene epoxide and 2-methyl-2-octanol:base being 0.8:0.2:9 or 1.8:0.2:9.

FIG. 6B is a graph of percent residual chlorine versus time in hours comparing the performance of hypochlorite solutions containing (i) DOWFAX® 2A1 versus (ii) AROMOX® DMMC-W using a 50:50 mixture of diisoamylene product produced according to Example II of application for U.S. Ser. No. 277,131 filed on June 25, 1981 and 2-methyl-2-octanol prepared according to Example I, supra, or not using any fragrance or essential oils with the weight ratio of AROMOX® DMMC-W:mixture of diisoamylene epoxide and 2-methyl-2-octanol:base being 3.8:0.2:9 and the ratio of DOWFAX® 2A1:diisoamylene epoxide-2-methyl-2-octanol mixture:base being 3.8:0.2:9.

Note 1: DOWFAX® 2A1 is a material consisting essentially of a mixture of compounds defined according to the structure:

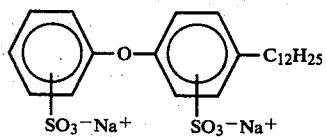

wherein the $C_{12}H_{25}$ moiety is branched chain and the $SO_3-Na+$ moieties are at various positions on each of the benzene rings.

EXAMPLE XIII

Dowfax® 3B2 (see Note 2, infra) in various quantities as set forth below, is mixed with 0.1 gram of 2-methyl-2-octanol prepared according to Example I. The resulting premixes are then added to 200 grams of an aqueous 7% sodium hypochlorite solution. Sufficient 12.5 M aqueous NaOH is added to bring the pH of the mixture up to 13.5. The following results are obtained:

| Percentage of DOWFAX® 3B2 | Clarity of hypochlorite solution after addition of premix |
|---|---|
| 0.23% | Clear after seven days |
| 0.15% | Clear after five days |
| 0.08% | Clear after three days |
| 0.01% | Clear after three days Initially slightly turbid; two phases exist after three days. |

When the 7% aqueous sodium hypochlorite solutions are used as laundry bleaches, the resulting laundry batches on dry-out in an atmosphere of 65% relative humidity yield substantially no characteristic "hypochlorite" odors but do have faint, pleasant "floral, citrusy" aromas. Furthermore, no such characteristic "hypochlorite" aromas are retained on the hands of the individuals handling such laundry batches in both the wet and the dry states.

Note 2: DOWFAX® 3B2 is a mixture of compounds essentially defined according to the structure:

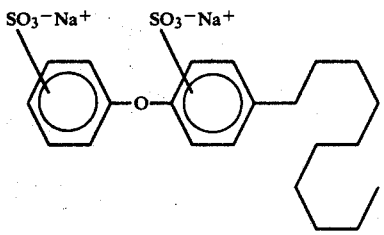

wherein the SO$_3$—Na+ moieties are at various positions on the phenyl moieties. Dowfax ® 3B2 is a registered trademark of the Dow Chemical Company of Midland, Mich.

In the following examples, Aromox ® DMC-W and Aromox ® DMMC-W are 30% aqueous solutions of dimethyl cocoamine oxide; and Aromox ® NCMDW is a 40% aqueous solution of N-cocomorpholine oxide produced by Armac Division of AKZO of Chicago, Ill.

EXAMPLE XIV

Four drops of a 25:75 wgt/wgt mixture of diisoamylene epoxide prepared according to Example II of application for U.S. Ser. No. 277,131 filed on June 25, 1981 and 2-methyl-2-octanol prepared according to Example I, supra, is added to 2 grams of Dowfax ® 3B2 and 0.5 grams of Aromox ® DMC-W to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "citrusy, floral" aroma with "woody/minty/eucalyptol-like" nuances. Furthermore, no such characteristic "hypochlorite" aroma is retained on the hands of the individual handling such laundry in both the wet and the dry states.

EXAMPLE XV

One gram of Dowfax ® 3B2; one gram of Dowfax ® 2A1 and 0.25 grams of Aromox ® DMMC-W is admixed with eight drops of 2-methyl-2-octanol prepared according to Example I. This premix is then added, with stirring to 200 grams of a mixture containing 4.5% aqueous sodium hypochlorite and 4.5% aqueous lithium hypochlorite. Sufficient 4 M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry on dry-out in an atmosphere of 50% relative humidity retains a "citrusy, floral" aroma; whereas without the use of the 2-methyl-2-octanol prepared according to Example I, supra, the bleached laundry has a faint characteristic disagreeable "hypochlorite" aroma.

EXAMPLE XVI

One gram of Dowfax ® 2A1 and one gram of Dowfax ® 3B2 is admixed with eight drops of a 50:50 mixture of one of the diisoamylene epoxide compositions of Example II of application for U.S. Ser. No. 277,131 filed on June 25, 1981 and 2-methyl-2-octanol. This premix is then added, with stirring to 200 grams of a mixture containing 4.5% aqueous sodium hypochlorite. Sufficient 4 M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry on dry-out in an atmosphere of 50% relative humidity retains a "citrusy, floral" aroma with "woody, eucalyptol and minty" nuances; whereas without the use of the perfume composition which is a mixture of diisoamylene epoxide and 2-methyl-2-octanol the bleached laundry has a faint characteristic disagreeable "hypochlorite" aroma.

EXAMPLE XVII 1.5 grams of Dowfax ® 2Al is admixed with eight drops of 2-methyl-2-octanol prepared according to Example I, supra. This premix is then added with stirring to 200 grams of a mixture containing 4.5% aqueous sodium hypochlorite and 4.5% aqueous lithium hypochlorite. Sufficient 2 M aqueous NaOH is added to bring the pH of the solution to 13.4. The mixture is then heated to 110° F. and maintained at that temperature with stirring for a period of two weeks. The resulting solution remains clear as a single phase when used as a laundry bleach. The resulting bleached laundry on dry-out in an atmosphere of 50% relative humidity, retains a "citrusy, floral" aroma, whereas without the use of the 2-methyl-2-octanol the bleached laundry has a faint characteristic disagreeable "hypochlorite" aroma.

EXAMPLE XVIII

Four drops of a 50:50 mixture of one of the diisoamylene epoxide mixtures produced according to Example II of application for U.S. Ser. No. 277,131 filed on June 25, 1981 and 2-methyl-2-octanol prepared according to Example I, supra, is added to 1.0 grams of Dowfax ® 3B2 and 0.25 grams of Aromox ® NCMD-W to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor, but does have a faint pleasant "floral, citrusy" aroma with "woody, minty, eucalyptol-like" nuances. Furthermore, no such characteristic "hypochlorite" aroma is retained on the hands of the individual handling such laundry in both the wet and the dry states.

EXAMPLE XIX

Four drops of 2-methyl-2-octanol prepared according to Example I, supra is added to 0.1 gram n-undecyl dimethyl amine oxide and 0.9 grams of Dowfax ® 3B2 to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor, but does have a faint pleasant "citrusy, floral" aroma. Furthermore, no such characteristic "hypochlorite" aroma is retained on the hands of the individual handling such laundry in both the wet and dry states.

EXAMPLE XX

Four drops of a 50:50 mixture of diisoamylene epoxide produced according to Example II of application for U.S. Ser. No. 277,131 filed on June 25, 1981 and 2-methyl-2-octanol prepared according to Example I, supra is added to 0.1 gram of n-dodecyl dimethyl amine oxide and 0.9 grams of Dowfax ® 2A1 to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "citrusy, floral" aroma with "woody, minty and eucalyptol-like" nuances. Furthermore, no such characteristic "hypochlorite" aroma is retained on the hands of the individual handling such laundry in both the wet and the dry states.

EXAMPLE XXI 0.2 grams of n-tridecyl dimethyl amine oxide and 0.7 grams of Dowfax ® 3B2 are admixed with eight drops of 2-methyl-2-octanol prepared according to Example I, supra. This premix is then added with stirring to 200 grams of a 7% aqueous solution of lithium hypochlorite. Sufficient 3 M aqueous LiOH is added to bring the pH of the solution of 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains a "citrusy, floral" atoma; whereas without the use of the 2-methyl-2-octanol bleached laundry has a faint characteristic disagreeable "hypochlorite" aroma.

EXAMPLE XXII

A mixture is prepared consisting of 39 grams of Dowfax ® 2A1 (60.75%); 4.5 grams of sodium palmitate (7.00%); and 20.7 grams of water (32.25%). The mixture is heated while stirring followed by ultrasonic dispersion thereby yielding a homogeneous gel. 64.2 grams of this material is used as follows: 4 drops of 2-methyl-2-octanol prepared according to Example I is added to 2.0 grams of the foregoing gel to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "citrusy, floral" aroma. Furthermore, no such characteristic "hypochlorite" aroma is retained on the hands of the individual handling such laundry in both the wet and the dry states.

EXAMPLE XXIII

A mixture is prepared consisting of 39 grams of Dowfax ® 2A1 (60.75); 4.5 grams sodium laurate (7.00%); and 20.7 grams of water (32.25%). The mixture is heated while stirring followed by ultrasonic dispersion thereby yielding a homogeneous gel. 64.2 grams of this material is used as follows: 4 drops of (a) one of the diisoamylene epoxide mixtures prepared according to Example II of application for U.S. Ser. No. 277,131 filed June 25, 1981 and (b) 2-methyl-2-octanol prepared according to Example I, supra, is added to 2.0. grams of the foregoing gel to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "citrusy, floral" aroma with "woody/minty/and eucalyptol-like" undertones. Furthermore, no such characteristic "hypochlorite" aroma is retained on the hands of the individual handling such laundry in both the wet and the dry states.

EXAMPLE XXIV

A mixture is prepared consisting of 20.1 grams Dowfax ® 2A1 (60.75%); 2.0 grams sodium palmitate (7.00%); and 20.0 grams of water (32.25%). The mixture is heated while stirring followed by ultrasonic dispersion thereby yielding a homogeneous gel. 64.2 grams of this material is used as follows: 4 drops of 2-methyl-2-octanol prepared according to Example I, supra, is added to 2.0 grams of the foregoing gel to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "citrusy, floral" aroma. Furthermore, no such characteristic "hypochlorite" aroma is retained on the hands of the individual handling such laundry in both the wet and the dry states.

EXAMPLE XXV

A mixture is prepared consisting of 10 grams of Dowfax ® 2A1 and 10 grams of Dowfax ® 3B2 (60.75%); and 2.0 grams of sodium laurate (7.00%); and 20.0 grams of water (32.25%). The mixture is heated while stirring followed by ultrasonic dispersion thereby yielding a homogeneous gel. 64.2 grams of this material is used as follows: 4 drops of 2-methyl-2-octanol produced according to Example I, supra, is added to 2.0 grams of the foregoing gel to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "citrusy, floral" aroma. Furthermore, no such characteristic "hypochlorite" aroma is retained on the hands of the individual handling such laundry in both the wet and the dry states.

EXAMPLE XXVI

A mixture is prepared consisting of 60 grams Aromox® DMMC-W, 30 grams Dowfax® 2A1; 6.0 grams lauric acid; 9.0 grams KOH; and 500 grams water. The mixture is heated while stirring followed by ultrasonic dispersion thereby yielding a homogeneous gel. 64.2 grams of this material is used as follows: 4 drops of 2-methyl-2-octanol is added to 2.0 grams of the foregoing gel to produce a clear premix. The clear premix is added to 200 grams of CLOROX® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "citrusy, floral" aroma. Furthermore, no such characteristic "hypochlorite" aroma is retained on the hands of the individual handling such laundry in both the wet and the dry states.

It is noteworthy that the viscosity of the solution subsequent to heating is 26.75 centipoises.

EXAMPLE XXVII

A mixture is prepared consisting of 60 grams of Aromox® DMMC-W, 21 grams of DOWFAX® 2A1; 3.6 grams of lauric acid; 10.5 grams of KOH and 508 grams of water. The mixture is heated while stirring followed by ultrasonic dispersion thereby yielding a homogeneous gel having a viscosity of 23.45 centipoises. 64.2 grams of this material is used as follows: 4 drops of a 50:50 mixture of (a) one of the diisoamylene epoxide mixtures produced according to Example II of application for U.S. Ser. No. 277,131 filed on June 25, 1981 and (b) 2-methyl-2-octanol produced according to Example I, supra, is added to 2.0 grams of the foregoing gel to produce a clear premix. The clear premix is added to 200 grams of CLOROX® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "citrusy, floral" aroma with "woody/herbaceous and eucalyptol-like" undertones. Furthermore, no such characteristic "hypochlorite" aroma is retained on the hands of the individual handling such laundry in both the wet and the dry states.

We claim:

1. A perfumed aqueous alkali metal hypochlorite solution comprising as a sole detergent a composition of matter selected from the group consisting of (1) at least one substance defined according to the structure:

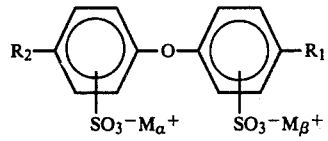

wherein at least one of $R_1$ and $R_2$ is $C_{10}$–$C_{12}$ straight chain or branched chain alkyl; when one of $R_1$ or $R_2$ is $C_{10}$–$C_{12}$ straight chain or branched chain alkyl the other of $R_1$ and $R_2$ is hydrogen; wherein $M_\alpha$ and $M_\beta$ are the same or different and each represents alkali metal selected from the group consisting of sodium, potassium and lithium and (2) a mixture comprising a material having the structure:

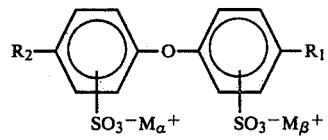

and intimately admixed therewith a substance having the structure:

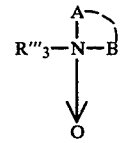

wherein $R_3'''$ is straight chain alkyl; wherein more than 55% of the $R_3'''$ moieties consist of straight chain alkyl having from 11 up to 13 carbon atoms and wherein "A" and "B" are each separately methyl up to 0.2% of one or more compatible perfume oils, said hypochlorite solution having a pH of 11 up to 14.0 and an aroma augmenting or enhancing quantity of 2-methyl-2-octanol.

2. The composition of matter of claim 1 which is thickened using a thickening quantity of $C_{10}$–$C_{20}$ alcanoic acid salt thickener in a concentration such that the viscosity of the composition is 20–60 centipoises at a temperature of 20°–40° C.

3. The composition of claim 1 wherein the compound having the structure:

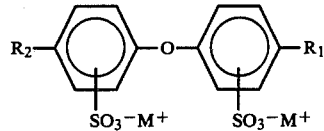

is selected from the group of materials having the structures:

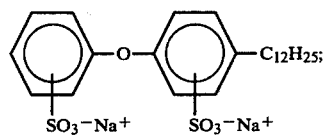

-continued

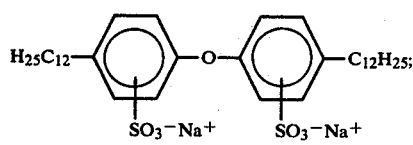

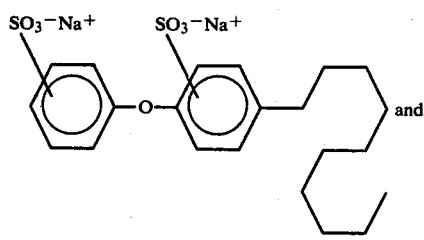

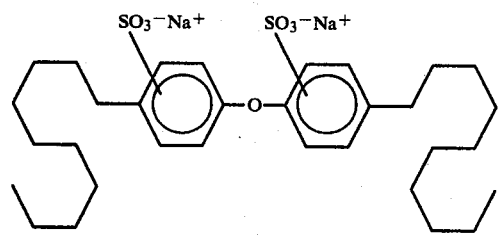

4. A process for producing a stable single phase aqueous alkaline metal hypochlorite solution having a pleasant fragrance consisting, in sequential order, of the steps of (a) adjusting the pH of an aqueous alkali metal hypochlorite solution to the range of 11–14.0; (b) admixing a composition of matter selected from the group consisting of: (i) a chemical compound having the structure:

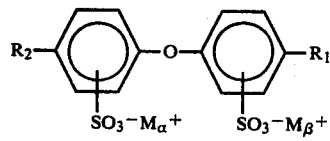

wherein at least one of $R_1$ and $R_2$ is $C_{10}$–$C_{12}$ straight chain or branched chain alkyl and $M_\alpha$ and $M_\beta$ are the same or different and each represents lithium, potassium or sodium and (ii) a mixture of at least one compound having the structure:

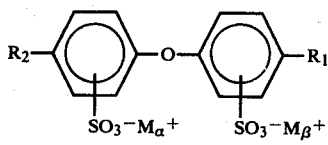

and a compound having the structure:

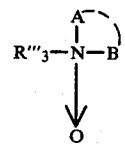

wherein $R_3'''$ is straight chain alkyl; wherein more than 55% of the $R_3'''$ moieties consist of straight chain alkyl having from 11 to 13 carbon atoms and wherein A and B are each separately methyl or taken together complete a morpholine ring with 2-methyl-2-octanol; and (c) adding said premix to the pH adjusted hypochlorite solution.

5. The process of claim 4 which includes the additional step prior to adding the premix to the pH adjusted hypochlorite solution of adding to the premix a gel-forming agent selected from the group consisting of sodium palmitate, lithium palmitate, potassium palmitate, sodium laurate, lithium laurate, potassium laurate, sodium stearate, potassium stearate and lithium stearate.

6. The composition of claim 1 wherein the thickening or gel-forming agent is selected from the group consisting of sodium laurate, potassium laurate, lithium laurate, sodium palmitate, potassium palmitate, lithium palmitate, sodium stearate, potassium stearate and lithium stearate.

7. The composition of claim 1 wherein in addition to 2-methyl-2-octanol as a perfuming material, there is also included diisoamylene epoxide.

8. The process of claim 4 wherein the perfuming material in addition to being 2-methyl-2-octanol also includes diisoamylene epoxide.

* * * * *